United States Patent [19]

Schroeppel

[11] Patent Number: 4,600,017
[45] Date of Patent: Jul. 15, 1986

[54] PACING LEAD WITH SENSOR

[75] Inventor: Edward A. Schroeppel, Miramar, Fla.

[73] Assignee: Cordis Corporation, Miami, Fla.

[21] Appl. No.: 632,625

[22] Filed: Jul. 19, 1984

[51] Int. Cl.⁴ ............................................. A61N 1/04
[52] U.S. Cl. ................................ 128/784; 128/419 P; 128/675
[58] Field of Search ..................... 128/419 P, 673, 675, 128/691, 692, 784, 785, 786

[56] References Cited

U.S. PATENT DOCUMENTS

| | | | |
|---|---|---|---|
| 2,976,685 | 3/1961 | Shipley | 128/675 |
| 3,242,449 | 3/1966 | Stedman | 128/675 |
| 3,358,690 | 12/1967 | Cohen | 128/419 |
| 3,490,441 | 1/1970 | Curtis | 128/675 |
| 3,614,954 | 10/1971 | Mirowski et al. | 128/419 D |
| 3,650,277 | 3/1972 | Sjostrand et al. | 128/419 C |
| 3,710,781 | 1/1973 | Huthcins, IV et al. | 128/675 |
| 3,811,427 | 5/1974 | Kresse | 128/675 |
| 3,815,611 | 6/1974 | Denniston, III | 128/419 D |
| 3,831,588 | 8/1974 | Rindner | 128/675 |
| 3,857,399 | 12/1974 | Zacouto | 128/419 P |
| 3,946,724 | 3/1976 | LaBalme | 128/675 |
| 4,003,370 | 1/1977 | Emil et al. | 128/673 |
| 4,140,132 | 2/1979 | Dahl | 128/419 PG |
| 4,191,193 | 3/1981 | Seo | 128/675 |
| 4,428,378 | 1/1984 | Anderson et al. | 128/419 PG |
| 4,456,013 | 6/1984 | DeRossi et al. | 128/675 |
| 4,485,813 | 12/1984 | Anderson et al. | 128/675 |

OTHER PUBLICATIONS

The Analysis and Interpretation of the Vibrations of the Heart, as a Diagnostic Tool and Physiological Monitor, C. M. Agress, et al., IRE Transactions on Bio-Medical Electronics, Jul. 1961, vol. BME-8, pp. 178-181.

A "New Dynamic Aspects of Amorphous Dielectric Solids", Hunklinger et al., Festerkorperprobleme XVI (1976), pp. 267-290.

The Piezoelectric Polymer $PVF_2$ and Its Applications, H. Sussner, 1979, Ultrasonics Symposium, Institute of Electrical and Electronic Engineers.

Primary Examiner—William E. Kamm
Attorney, Agent, or Firm—Henry W. Collins; Thomas R. Vigil

[57] ABSTRACT

The pacing lead with sensor is adapted to be inserted into a human heart and includes a piezoelectric device, such as a bimorph, for sensing the occurrence of a phenomenon in the heart. The piezoelectric device can be positioned in the heart while the signal it generates is carried outside the heart, where it can be utilized. The piezoelectric device of the present invention is designed to indicate a phenomenon occurring, and can measure the absolute and/or relative value of the phenomenon such as pressure. As a result, the piezoelectric device utilized is easy to construct and manufacture, and may be used without complicated equipment.

15 Claims, 9 Drawing Figures

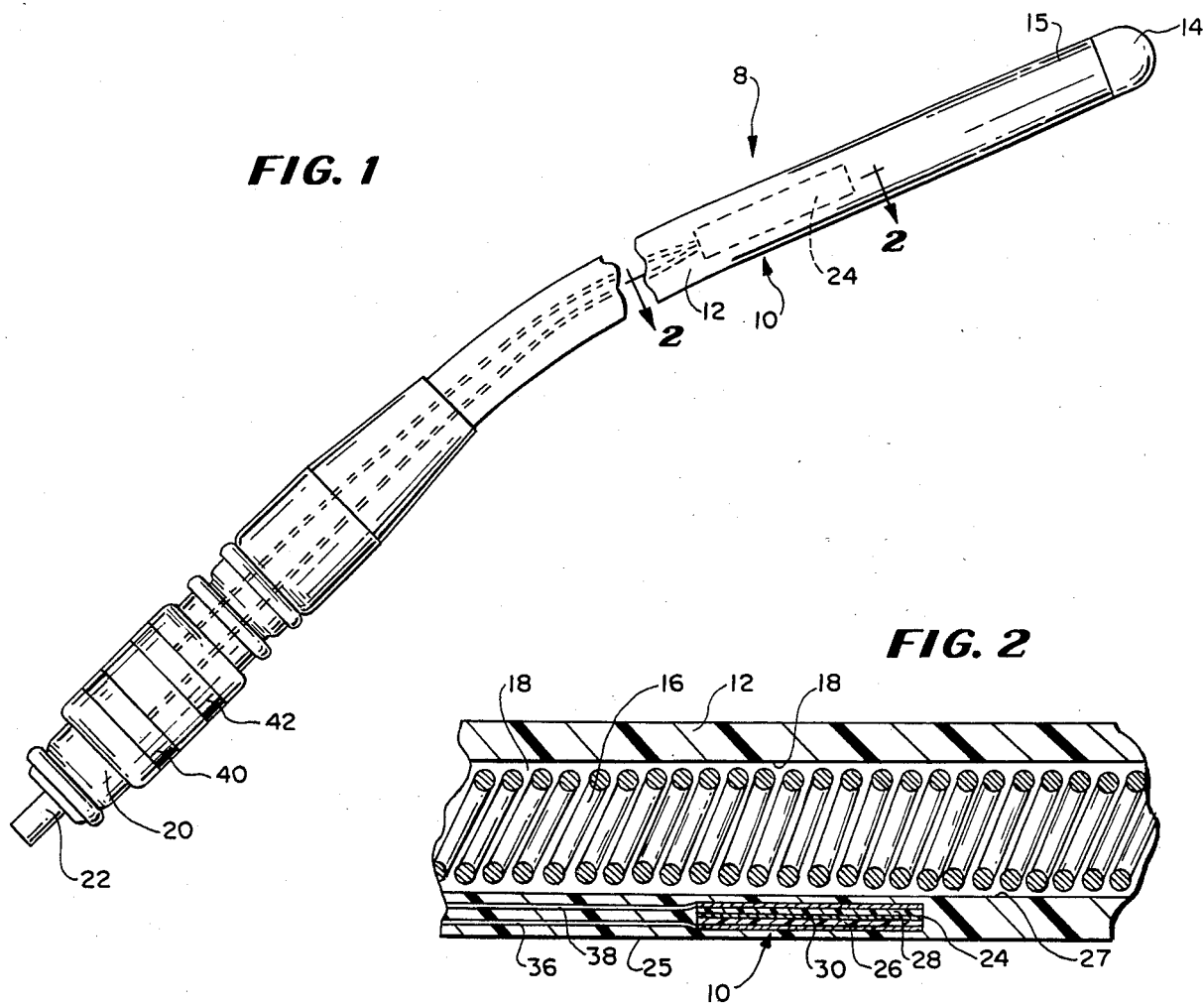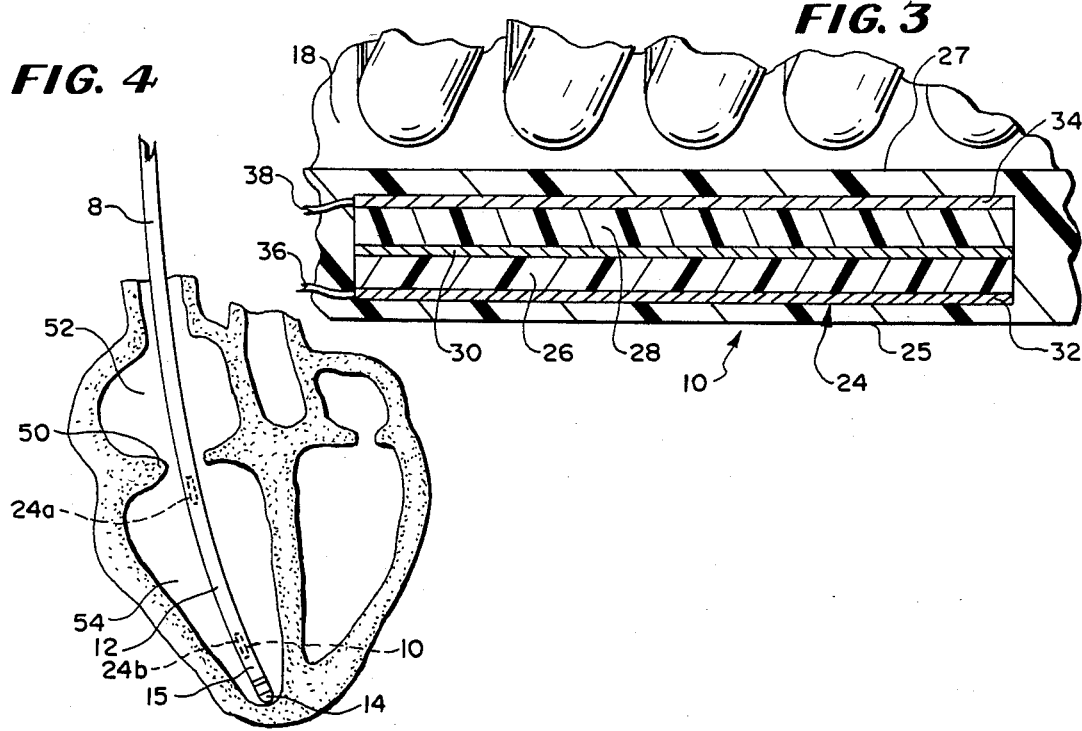

PACING LEAD WITH SENSOR

BACKGROUND OF THE INVENTION

1. Field of the Invention

This invention relates to a pacing lead with sensor mounted therein for measuring the occurrence of a phenomenon in a living organism, and more particularly, to a pacing lead having a piezoelectric sensor, the pacing lead being implanted in a living organism whereby the phenomenon acting on the sensor will generate an electric waveform indicative of the phenomenon. The phenomenon sensed is typically contractions of the heart.

2. Description of the Prior Art

Heretofore, various sensors have been developed for sensing phenomena occurring in living organisms, and particularly, the human body and heart. For example, cardiac sensors are disclosed in U.S. Pat. Nos. 2,634,721; 3,038,465; 3,490,441; 3,811,427 and 3,831,588. These sensors have utilized various complicated constructions, such as strain gauges in U.S. Pat. Nos. 2,976,865 and 4,003,370, field effect transistors in U.S. Pat. No. 3,946,724, PN type transducers in U.S. Pat. No. 3,710,781, and signal generating semiconductor devices in U.S. Pat. No. 3,811,427.

Further, it has been experimentally suggested to use piezoelectric sensors for measuring heart beats and blood flow by wrapping a band of piezoelectric material around a patient's chest or leg, including those of the ferroelectric polymer and polyvinylidene fluoride (PVF$_2$) types. For example, see "Ferroelectric Polymers and their Application" by Michael A. Marcus, appearing in Ferroelectrics: 40, 1982, and "Piezoelectric High Polymer Foils as Physiological Mechanic-Electric Energy Converters" by E. Hausler, H. Lang and F. J. Schreiner, appearing in IEEE 1980 Bio Medical Group Annual Conference, Frontiers of Engineering in Health Care.

Further, it is known to implant a piezoelectric device in a living organism for other purposes, such as to: power a cardiac or other pacer as suggested in U.S. Pat. No. 3,659,615, and control or vary the pacing rate with the implantee's own physical activity as disclosed in U.S. Pat. No. 4,140,132.

It has also been known that under controlled clinical conditions one can, by placing a microphone on the chest of a person, measure the vibrations of the heart and obtain graphs of waveforms showing, at a minimum, the opening and closing of the heart valves. See, for example, "The Analysis and Interpretation of the Vibrations of the Heart, as a Diagnostic Tool and Physiological Monitor" by C. M. Agress, M. D. and L. G. Fields appearing in IRE Transactions on Biomedical Electronics, July 1961.

As will be described in greater detail hereinafter, it has been found from studies on dogs using a pacing lead having a piezoelectric sensor mounted in the distal end portion thereof in accordance with the teachings of the present invention, that graphs of waveforms can be obtained clearly showing the opening and closing of the heart valves. This can be significant since from measurements of opening and closing of the heart valves, one can determine stroke volume and then by multiplying stroke volume by heart rate, one can determine cardiac output.

SUMMARY OF THE INVENTION

The pacing lead with piezoelectric sensor of the present invention is simply and easily constructed, and comprises a simple piezoelectric sensor located directly within the body of a lead or catheter adapted for placement in a living organism, such as a human heart. The lead piezoelectric sensor of the present invention has a stress imposed thereon by the phenomenon, e.g. heart contraction or changes in pressure of the blood in the heart, and generates an electric waveform indicative of the sensed phenomenon, e.g. heart contraction or pressure of blood.

The sensor is preferably a piezoelectric bimorph, or if desired, can utilize a piezoelectric polymer film construction, incorporated directly in an elongated lead or catheter body. The material selected for the catheter body is such so as not to unduly inhibit the transmission of the signal caused by the phenomenon to the bimorph. Further, as the sensor is implanted or placed in or close to the heart, the signal received from the lead and the waveform generated at the sensor are less susceptible to extraneous electrical noise.

BRIEF DESCRIPTION OF THE DRAWINGS

FIG. 1 is a plan view of a pacing lead with sensor constructed according to the teachings of the present invention.

FIG. 2 is an enlarged cross-sectional fragmentary view of the lead with sensor shown in FIG. 1 and is taken along line 2—2 of FIG. 1.

FIG. 3 is a further enlarged fragmentary view of a portion of FIG. 2.

FIG. 4 is a cross-sectional view of a human heart showing the pacing lead with sensor inserted into the heart.

DESCRIPTION OF THE PREFERRED EMBODIMENT

Figure 5:
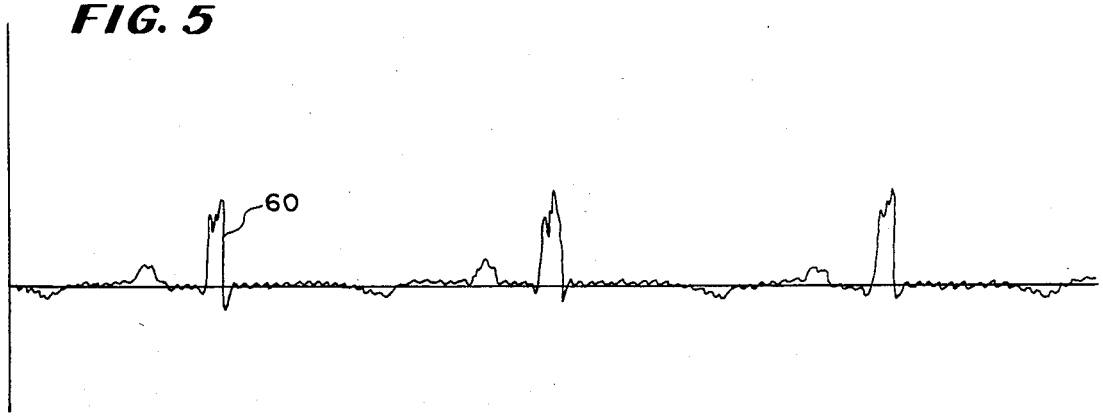
FIG. 5 illustrates an electrocardiogram (EKG) generated by the action of a dog's heart.

Referring to FIG. 1, there is illustrated therein a unipolar pacing lead 8 having a sensor 10 incorporated into a catheter body 12 of the lead 8. The catheter body 12 is of conventional length and size or diameter and is capable of being inserted into an appropriate blood vessel for insertion to a desired position in a heart. A tip electrode 14 is mounted at distal end 15 of the lead 8. Of course, if desired, bipolar pacing electrodes can be provided on or near the distal end of the lead 8.

As is conventional, the pacing tip electrode 14 is connected by a coiled wire conductor 16 (FIG. 2) within the conventional hollow center of lumen 18 (FIG. 2) of the catheter body 12. The coiled wire conductor 16 extends from the distal end 15 to a proximal end 20 (FIG. 1) of the lead 8 where it is connected to pin electrode 22 adapted to be inserted into a conventional pacemaker or, if desired, other electronic circuitry.

The sensor 10 is preferably incorporated directly into the body 12 of the lead 8, which as is conventional, may be made of a medical grade silicone rubber, polyurethane, or the like. Preferably, the sensor 10 is in the form of a piezoelectric bimorph 24 located between an outer wall 25 of the lead 8 and an inner cylindrical surface 27 defining a wall surface 27 of the lumen 18. The bimorph 24 as shown in FIG. 3, has a pair of ceramic sheets 26 and 28 made of suitable piezoelectric materials, such as barium titanate, lead titanate zirconate, lead metaniobate and/or sodium bismuth titanate. As is conventional, the piezoelectric sheets 26 and 28 are separated by a shim 30 of material such as brass. Such a suitable bimorph 24 can be obtained from Piezoelectric Products Inc., or from Vernitron Piezoelectric Division. The bimorph's upper and lower surfaces 32 and 34 are composed of fired on silver or electroless nickel to which a pair of insulated wires 36 and 38 are secured, such as by silver soldering, welding, crimping, or with conductive adhesive. These wires 36 and 38 are incorporated in the body 12 and extend to the proximal end 22, wherein they are similarly connected to a pair of ring or sleeve connectors 40 and 42 (FIG. 1). From there, conventional ring connectors in a socket of a pacer (not shown) will connect the sleeves 40 and 42 to appropriate electronic circuitry in the pacer.

The exact placement of the bimorph 24 along the length of the lead 12 is dependent upon what is desired to be monitored. For example, if the sensor 10 is to monitor the activity of the tricuspid valve 50 (FIG. 4) between the right atrium 52 and the right ventricle 54, the bimorph 24 would be placed a distance of approximately 7 to 8 centimeters from the distal end of the lead 8 to be just below the tricuspid valve as shown by sensor 24a in FIG. 4. If, for example, the pressure of blood in the ventricle is to be monitored, the bimorph 24 would be placed closer to the distal end 15, say 1 to 3 centimeters, so that it will be located well within the ventricle 54 and just above the apex or bottom of the ventricle 59 as shown by sensor 24b in FIG. 4. Likewise, if the interest was the pressure of blood in the atrium 52, the bimorph 24 could be placed even farther from the distal end, say 9 to 11 centimeters therefrom, so as to be located in the atrium 52.

It is important to note that the bimorph 24 is totally encapsulated within the lead body 12, so that it is isolated from the blood, and yet is still able to sense any pressure changes as a result of the opening and closing of the tricuspid valve 50. This is because the bimorph 24, rather than measuring an accurate absolute pressure, functions somewhat like a microphone, or more like a sonar pickup, to pick up pressure pulses and waves generated by the opening and closing of the tricuspid valve 50, and travelling through the blood, through the encapsulating silicone rubber to the bimorph 24, where it stresses the same and generates an electrical waveform. The encapsulation material is such that pressure pulses or waves can travel therethrough and be transmitted to the bimorph, recoverably stressing the same, to generate electrical waveform signals. Preferably, the wall thickness of the catheter body is less than one millimeter and the thickness of the encapsulation material on the outer facing surface of the bimorph 24 is less than 0.2 millimeter so as to not unduly diminish the pressure pulse or wave to be sensed.

The lead 8 with sensor 10 (bimorph 24) lends itself to telemetering of the waveform for waveform analysis, and to interpretation analysis and utilization of the waveform for determining cardiac parameters, such as cardiac output.

In FIG. 5 is shown a copy of an electrocardiogram (EKG) 60 generated by the action of a dog's heart. The waveform 60 is an electrocardiogram of the electrical activity of the dog's heart occurring during a ventricular contraction.

Figure 6:
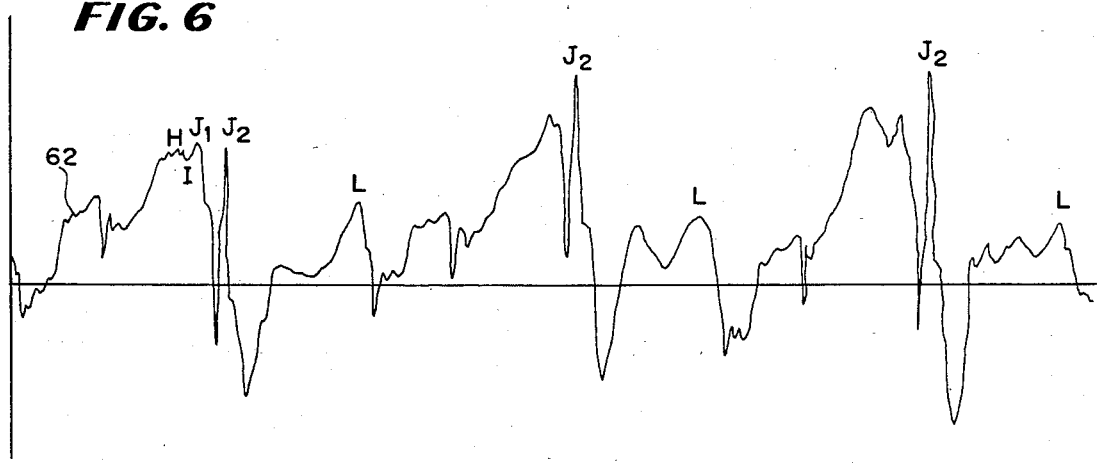
FIG. 6 is a graph of the waveform generated by the sensor in the lead shown in FIG. 1 when the sensor is located just above the apex of the right ventricle, and shows the opening and closing of the semilunar valves in the heart correlated with the EKG activity shown in FIG. 5.

In FIG. 6 is shown, a waveform 62 generated by and recorded from the bimorph 24b located just above the apex of the ventricle 54.

The waveform 62 shows several important heart functions. In this respect, $J_2$ marks the opening of the semilunar valve and L marks the closure of the semilunar valve. Also, the H wave of the vibrocardiogram or waveform 62 occurs simultaneously with the onset of left ventricular isometric contraction.

In animal studies, such a waveform or vibrocardiogram 62 obtained with a microphone, correlated very well with periods of heart activity measured more accurately with other methods. For example, H–$J_2$ equals the period of isometric contractions; $J_2$–L equals ejection time; H–L equals systole; L–H equals diastole; and $J_1$–$J_2$ equals rapid ventricular ejection.

One of the important periods is the ejection time, $J_2$–L since this period can be used to determine stroke volume which is then used to determine cardiac output so that a doctor can determine the effectiveness of the ventricular, atrial or dual atrial-ventricular pacing in assisting cardiac output.

In this respect, it has been determined that stroke volume times heart rate equals cardiac output. Here, reference is made to the article "Measurement of Stroke Volume by the Vidrocardiogram" by Agress et al which appeared in the December 1967 issue of Aerospace Magazine. From the studies made by Agress et al, it has been found that:

Stroke volume $(SV) = 0.32(J_2-L) - 19.9$

Similarly, changes in stroke volume can be defined as follows:

$\Delta(SV) = 0.30[\Delta(J_2-L)] + 0.63$

If desired, the isovolumetric contraction time (H–$J_2$) can be included in the determination of stroke volume using the vibrocardiogram although it is not certain that one can obtain a more accurate determination of stroke volume by utilizing H–$J_2$ as well as $J_2$–L time periods.

Again, stroke volume times heart rate yields cardiac output, a well established indication of heart pumping effectiveness and the pacing of the heart to assist heart pumping.

Figure 7:
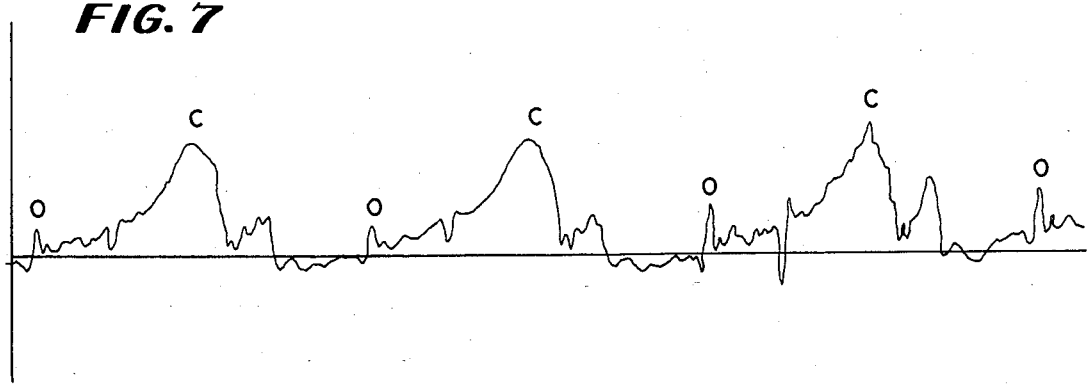
FIG. 7 is a graph similar to the graph of FIG. 5 of the waveform generated by the sensor when it is located just below the tricuspid valve correlated with the EKG activity shown in FIG. 5.

FIG. 7 is a waveform 64 which is generated by sensor 24a located just above the tricuspid valve 50. Although not known with absolute certainty, it is believed that O represents opening of the tricuspid valve and C represents closing of the tricuspid valve.

The sensor 10 of the present invention can be used to measure absolute and/or relative values of the phenomena being sensed, such as valve openings and closings, by viewing the resultant waveforms or traces 62 or 64 obtained with the bimorphs 24b or 24a located at various positions in the heart and such waveforms provide useful and valuable information. The comparison between various generated traces provides a physician with a powerful tool in analyzing any changes in a patient's condition, e.g., change in ejection time. The primary phenomenon measured in a heart is the change in blood pressure in one of the heart chambers as the heart contracts and expands.

Figure 8:
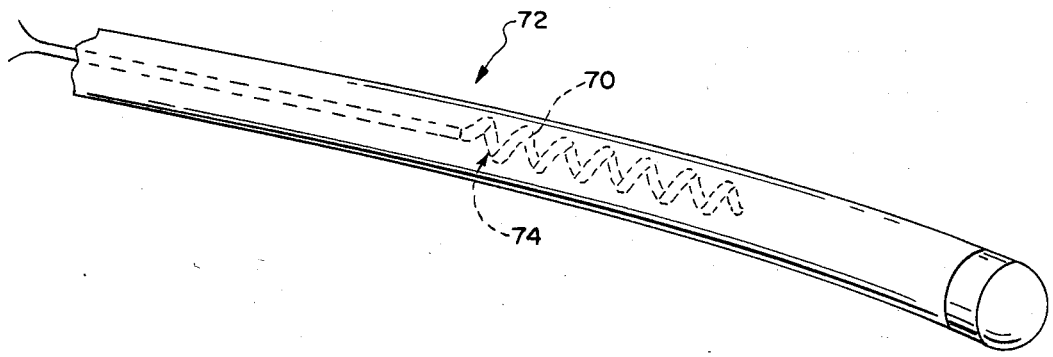
FIG. 8 is a perspective view of a distal end portion of a pacing lead and shows a sensor therein in the form of a thin film polymer piezoelectric strip mounted in a spiral or corkscrew configuration in the pacing lead distal end portion.

Also, the sensor 10 of the present invention can be made in other forms than a piezoelectric bimorph 24. In this respect, the sensor 10 can be realized by a piezoelectric strip 70 constructed of a thin film polymer, e.g. polyvinylidene fluoride ($PVF_2$) and mounted in a pacing lead distal end portion 72 in a spiral or corkscrew configuration 74 as shown in FIG. 8.

Figure 9:
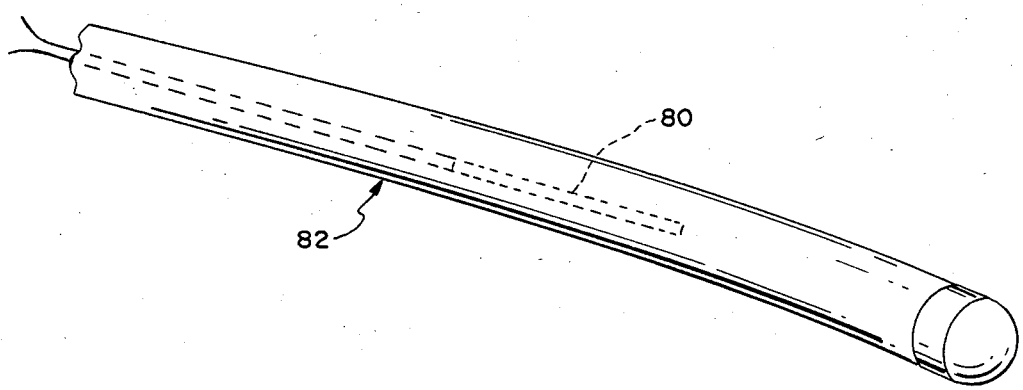
FIG. 9 is a perspective view of a distal end portion of a pacing lead and shows a sensor therein in the form of a thin film polymer piezoelectric elongate strip mounted coaxially of the pacing lead distal end portion.

Alternatively, a straight piezoelectric strip 80 constructed of a thin film polymer, e.g. polyvinylidene fluoride ($PVF_2$) can be used for the sensor 10 and mounted in and coaxially of the elongate axis of a pacing lead distal end portion 82 as shown in FIG. 9.

Of course, the sensor 10 of the present invention can be designed for monitoring other cardiac functions besides changes in blood pressure, such as monitoring atrial or ventricular contractions, opening or closing of other cardiac valves, measuring blood turbulence, or other cardiac activity. Also, the sensor 10 can be incorporated in other than a cardiac lead 8, and could be used to sense phenomena occurring in various parts of the body, such as in the ventricles of the brain or the urinary bladder.

Also, it will be understood that the waveforms obtained can be analyzed by a microprocessor in a body implanted pacemaker or pacer or in an external signal processing circuit and the openings and closings of particular valves, e.g., semilunar valves or tricuspid valves, in the heart can be determined and this information can be utilized for controlling the pacing pulses, particularly the rate thereof, supplied to the electrode 14.

While one preferred embodiment of a pacing lead 8 with a sensor 10 has been illustrated and described above, it is to be understood that variations and modifications and equivalent structure can be made without departing from the teachings of the present invention. Accordingly, the scope of the invention is only to be limited as necessitated by the accompanying claims.

I claim:

1. An integral pacing lead comprising: a flexible lead body having a generally cylindrical outer wall surface, a lumen within and extending the length of said lead body, a given wall thickness, a proximal end, a proximal end portion, a distal end, and a distal end potion; a tip electrode mounted at said distal end of said lead body for pacing a heart muscle; a pacer terminal pin extending from said proximal end of said lead body; first and second spaced apart metallic sleeve connectors on said proximal end portion; a pacer wire conductor within said lumen of said lead body and having a distal end connected to said tip electrode and a proximal end adapted to be connected to a pacer through said pacer terminal pin; piezoelectric pressure sensing means mounted in said lead body distal end portion adjacent to said outer wall surface and at a pre-determined distance behind said tip electrode for generating, from inside the heart, a waveform of heart activity in response to changes in right ventricular blood pressure, said waveform showing openings and closings of the tricuspid valve in the right ventricle of a heart when said lead body distal end portion is received in the right ventricle of a heart; and first and second wire conductors in said lead body, each wire conductor having a distal end connected to said piezoelectric pressure sensor means and a proximal end connected to said first or second sleeve connector; said sleeve connectors being electrically isolated from each other and electrically isolated from said pacer terminal pin, and being adapted to be received in a socket in a pacer and to make contact with ring connectors positioned in the socket.

2. The lead of claim 1 wherein said piezoelectric pressure sensing means are a piezoelectric bimorph which generates an electrical waveform as the blood pressure changes due to opening and closing of a heart valve.

3. The lead of claim 2 wherein said lead body is made of an elastomeric material such as silicone, polyurethane, or the like, and said bimorph comprises at least two sheets of material and a brass shim therebetween, said sheets of material being selected from the class consisting essentially of: barium titanate, lead titanate zirconate, lead metaniobate, and sodium bismuth titanate.

4. The lead of claim 1 wherein said pressure sensing means are located 1 to 3 centimeters behind said tip electrode.

5. The lead of claim 1 wherein said pressure sensing means are located 7 to 8 centimeters behind said tip electrode.

6. The lead of claim 1 wherein said pressure sensing means are located 9 to 11 centimeters behind said tip electrode.

7. The lead of claim 1 wherein said lead body has a wall thickness which is less than 1 millimeter.

8. The lead of claim 7 wherein said piezoelectric pressure sensing means are mounted in said wall of said lead body and a layer of flexible encapsulating material covers said piezoelectric pressure sensing means, and isolates said piezoelectric pressure sensing means from the blood, said layer having a thickness of less than 0.2 millimeter.

9. The lead of claim 8 wherein said layer of encapsulating material is made of polyurethane.

10. The lead of claim 8 wherein said layer of encapsulating material is made of silicone rubber.

11. The lead of claim 1 wherein said piezoelectric pressure sensing means are totally encapsulated within said flexible lead body.

12. The lead of claim 1 wherein said piezoelectric pressure sensing means are of the polymeric ferroelectric type.

13. The lead of claim 1 wherein said piezolelectric pressure sensing means utilize a polyvinylidene fluoride film construction.

14. The lead of claim 1 wherein said piezoelectric pressure sensing means are located approximately 1-3 centimeters behind said tip electrode so as to be located above the apex of the right ventricle when said lead body distal end portion is received in a right ventricle.

15. The lead of claim 1 wherein said piezoelectric pressure sensing means are located a sufficient distance of approximately 7-8 centimeters behind said tip electrode so as to be located just below the tricuspid valve in the right ventricle when said lead body distal end portion is received in a right ventricle.

* * * * *